(12) United States Patent
Mombrinie

(10) Patent No.: US 7,901,389 B2
(45) Date of Patent: Mar. 8, 2011

(54) LIQUID REMOVAL METHOD AND APPARATUS FOR SURGICAL PROCEDURES

(75) Inventor: Bruno Mombrinie, Santa Rosa, CA (US)

(73) Assignee: AVEC Scientific Design Corporation, Windsor, CA (US)

( * ) Notice: Subject to any disclaimer, the term of this patent is extended or adjusted under 35 U.S.C. 154(b) by 1097 days.

(21) Appl. No.: 10/794,281

(22) Filed: Mar. 3, 2004

(65) Prior Publication Data
US 2005/0197639 A1   Sep. 8, 2005

(51) Int. Cl.
*A61M 1/00* (2006.01)
(52) U.S. Cl. .......................................... 604/317; 604/329
(58) Field of Classification Search .......... 604/304–308, 604/317–322, 327–329
See application file for complete search history.

(56) References Cited

U.S. PATENT DOCUMENTS

| | | | | |
|---|---|---|---|---|
| 5,244,457 A | * | 9/1993 | Karami et al. | 602/55 |
| 5,549,584 A | * | 8/1996 | Gross | 604/313 |
| 5,678,564 A | * | 10/1997 | Lawrence et al. | 600/574 |
| 6,355,858 B1 | * | 3/2002 | Gibbins | 602/41 |
| 6,685,681 B2 | * | 2/2004 | Lockwood et al. | 604/305 |
| 7,128,735 B2 | * | 10/2006 | Weston | 604/543 |

OTHER PUBLICATIONS

PCT International Search Report for PCT/US2005/00007397.

* cited by examiner

*Primary Examiner* — Michele Kidwell
(74) *Attorney, Agent, or Firm* — Gary Hoenig

(57) ABSTRACT

The present invention relates to an improved apparatus and method for aspirating liquids from surfaces particularly during medical procedures. Apparatus for removing liquid from a surface in the region of a medical procedure such as an operating room floor responsive to a drawn vacuum of preselected magnitude includes a plenum with an interior volume defined by an elongated box element with a plurality of supports member integral thereto or by an elongated tube, the plenum being perforated so as the exterior of the plenum is in direct liquid communication with the interior of the plenum, an absorptive wicking pad secured to the plenum so as to cover the perforations, an a vacuum conduit tube in direct vacuum communication with a vacuum collection system. A method of removal of liquids standing on surfaces such as operating room floors accomplished by positioning the disposable liquid removal apparatus with the exposed absorptive wicking pad down into the liquid, attaching the apparatus to a vacuum collection system, activating the system, and repositioning the apparatus as required.

12 Claims, 3 Drawing Sheets

LIQUID REMOVAL METHOD AND APPARATUS FOR SURGICAL PROCEDURES

BACKGROUND OF INVENTION

The present invention relates in general to the field of removal and collection of liquids from surfaces as generated by medical procedures. More particularly, this invention relates to a disposable absorptive apparatus and method for wicking, collecting and transporting surgically generated or other medical procedure associated liquids from surfaces for use with a vacuum driven fluid collection system.

Many medical procedures generate significant volumes of fluid from the procedure site. Some procedures flush the procedure site with various liquids to introduce agents such as antiseptics or to flush debris away from the site. Additionally liquids may be released from the patient. Liquids expelled from the medical procedures collect at various locations such as the operating table and particularly on the floor. During arthroscopy surgery as typically performed on the knee, significant quantities of liquid are often expelled from the surgical region and collect on surrounding surfaces, particularly the floor. The potentially hazardous nature of the liquids precludes draining the floor, instead the liquids are collected. Liquids tend to puddle on the floor causing a trip and bio hazard for the operating room personnel.

During operations, suction devices are installed to remove liquids that have collected. Apparatus including a suction head for aspirating liquid from an operating room floor include mats as shown in U.S. Pat. No. 5,827,246, entitled "Vacuum Pad for Collecting Potentially Hazardous Fluids", and in U.S. Pat. No. 4,729,404, entitled "Receptacle for Collecting Fluid". The vacuum driven mats are so engineered as to remove liquids that collect on top of the mat presenting a disadvantage. The mats further require significant air flow through the apparatus to maintain a vacuum sufficient to draw fluids into the system. Suction devices that require high air flow produce noise levels that can interfere with communication in the operating room. Mats are typically designed to remain stationary on the floor thereby requiring a number of mats to collect liquids in other areas of the operating room. Additionally, mats are generally costly as compared to other liquid remove systems such as towels.

Another type of liquid removal apparatus using a flat plate suction head spaced away from the surface where the liquid resides is typified by U.S. Pat. No. 5,014,389, entitled "Foot Manipulated Suction Head and Method for Employing Same", U.S. Pat. No. 5,655,258, entitled "Device for Aspirating Fluids from Hospital Operating Room Floor", and U.S. Pat. No. 6,136,098, entitled "Method for Aspirating Fluid from An Operating Room". The flat plate suction head is characterized by a flat plate positioned away from the surface where the liquid resides by spacers thereby permitting liquids to collect in the gap between the floor and the apparatus. When liquid is not present, air is drawn through the apparatus resulting in increased load on the vacuum collection system and higher noise levels. Apparatus placement can be accomplished; however, the potential trip hazards presented to the operating personnel are still present due to the size of the apparatus.

A further apparatus is as described in U.S. Pat. No. 5,380,278, entitled "Liquid Cleansing and Evacuation Method and Apparatus for Use in Surgical Procedures" utilizes an annular suction ring for continuously evacuating fluid from a surgical area.

Devices in the sterile field of an operating room, for example, must be either be sterilized or replaced after each operation. Sterilizing is typically a costly process and therefore a low cost disposable apparatus is preferable. High cost is a significant disadvantage of many of the prior art solutions.

Vacuum collection systems are often installed in medical procedure areas, particularly operating rooms. In the operating room, the vacuum collection system provides a vacuum draw for numerous devices collecting liquids. When no liquid is presented to many suction driven liquid removal devices, the load on the vacuum collection system increases and can compromise the system.

Trip hazards are reduced by designs that incorporate a low profile on the surface and can be stepped on or crushed without detriment to the operation of the apparatus.

Prior to the present invention there existed a need for an improved liquid removal apparatus and method that is low cost, disposable, low profile, low noise, low load on the vacuum collection system to address disadvantages of the prior art.

SUMMARY OF INVENTION

Accordingly, the present invention is directed to removal and collection of liquids from surfaces as generated by medical procedures and, more specifically, to a disposable liquid removal apparatus with low manufacturing costs, improved performance and user conveniences, substantially reducing or eliminating other disadvantages of the prior art.

The present invention includes a liquid removal suction apparatus generally comprising in combination: a plenum with a plurality of perforations on one side of the plenum with an absorptive wicking pad attached to the side of the plenum with the perforations and a flexible vacuum conduit tube for connection to a vacuum collection system typically found in areas where medical procedures are performed for collecting fluids expelled from the region of the procedure.

The apparatus draws liquids, from a surface upon which it is positioned, into an absorptive wicking pad principally by means of wicking or capillary effects of the wicking pad material.

As the absorptive wicking material of the pad draws standing fluids into the material reducing air flow through the wicking material, thereby presenting a vacuum on the surfaces of liquids retained in the wicking material. The retained fluids, now filling the voids in the wicking material restrict the air flow to the perforations essentially forming fluid seals around the perforations. The absorbed liquid is drawn by a vacuum into a plenum fixed to the top side of the absorptive wicking pad through small perforations in the plenum surface fixed to the absorptive pad. The vacuum present in the plenum then draws both the retained fluids and entrained air into the plenum. However, the small size of the perforations limit the total flow of air into the plenum. The small size of the perforations also permit highly efficient transfer of liquids through to the plenum as limited leakage of air through other perforations not presented with liquid limit the amount the vacuum in the plenum is compromised. Fluid collected within the plenum is evacuated by means of the vacuum in the connecting tube running to the operating room vacuum collection system.

Because the required air mass flow rates through the apparatus are low and the pressure differential between atmosphere and the plenum pressure is low, both the inside diameter and wall thickness of the vacuum supply hose can be small. Reducing the inside diameter and wall thickness correspondingly reduces the material costs for the component. The low air mass flow rate also minimizes the load on the operating room vacuum collection system. A further advantage of the small diameter tube is to facilitate the ease of positioning of the apparatus. Prior art devices require larger diameter and thicker supply tubes to accommodate high air mass flow rates and lower pressures so as not to collapse and is resistant damage from being stepped upon.

Many prior art devices draw considerable volumes of air when fluid is not presented to the device thereby potentially compromising the vacuum collection systems.

The invention being generally dimensioned to be typically 2 feet long and about 4 inches wide with a vertical height of less than 1 inch, the apparatus does not obstruct movement in the operation room. Plenum construction is also resistant to crushing from being stepped upon. The long dimension has an addition advantage in that the invention may be used as a barricade to liquids flowing across the surface.

A still further advantage of the present invention is that the total surface area from which the apparatus can recover standing fluid is large without necessitating large or multiple devices such as mats. And the present invention is also easy to reposition.

Another aspect of the invention is a method of removing liquid from surfaces for use in surgical procedures. The method of liquid removal apparatus is to position the pad in standing water on a surface with the exposed absorptive wicking pad facing the surface, the flexible vacuum conduit tube is secured to the vacuum collection system in the operating room and the vacuum collection system is activated.

BRIEF DESCRIPTION OF DRAWINGS

The accompanying drawings, which are incorporated in and constitute a part of this specification illustrate embodiments of the invention and, together with the description, serve to explain the features, advantages, and principles of the invention.

In the drawings.

DETAILED DESCRIPTION

Figure 1:
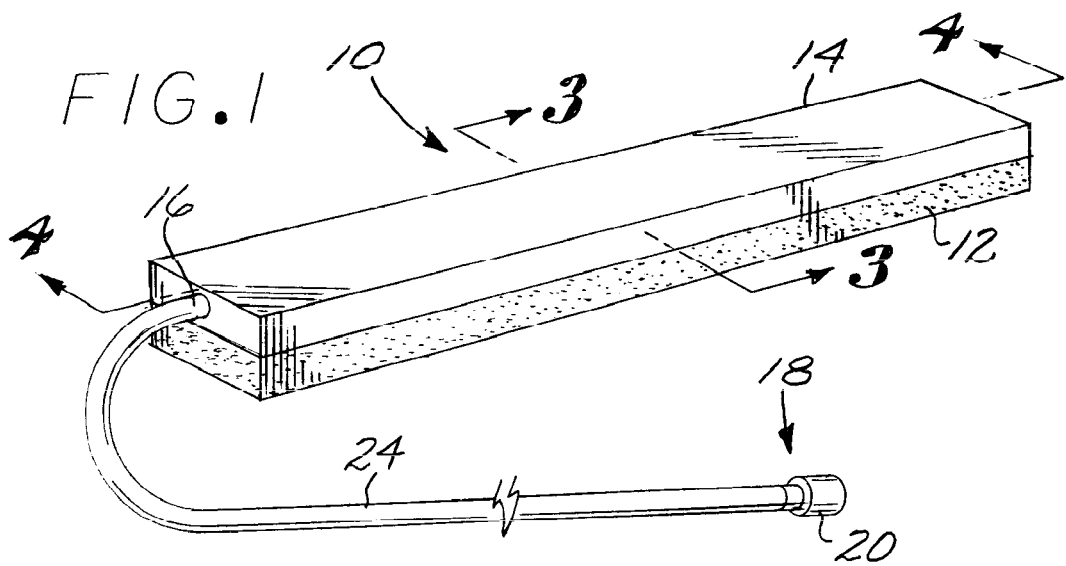
FIG. 1 is a perspective view of an embodiment of the disposable liquid removal apparatus constructed in accordance with this invention when arranged so as to clearly illustrate the components of the invention.
Figure 2:
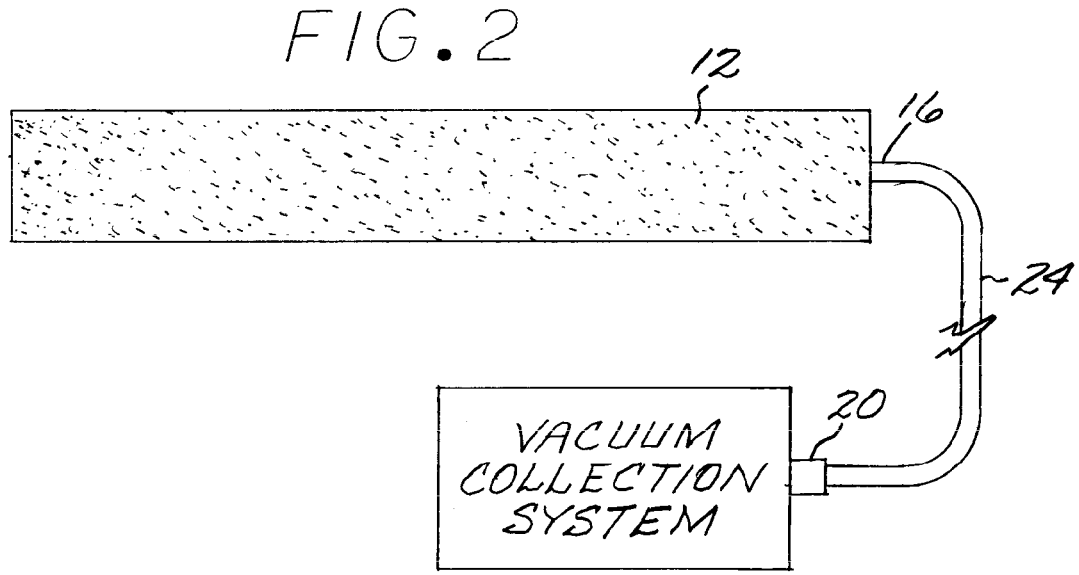
FIG. 2 is a schematic drawing showing the bottom view of a liquid removal apparatus attached to a vacuum collection source.

Although particular embodiments of the invention have been described in detail for purposes of illustration, various modifications may be made without departing from the spirit and scope of the invention. Accordingly, the invention is not to be limited except as by the appended claims. Referring now in greater detail to the various figures of the drawing wherein like reference characters refer to like parts, there is shown at 10 in FIG. 1, liquid removal apparatus constructed in accordance with the subject invention. Before describing the details of that apparatus it must be pointed out that while the apparatus is particularly suited for liquid removal from surfaces such as found in operating rooms, it can also be used of other similar environments requiring similar liquid removal functions.

A preferred embodiment of the apparatus for the liquid removal from surfaces in the region of medical procedures is designated generally 10 in FIG. 1 showing components including an absorptive wicking pad 12 fixed to the bottom of a plenum 14. A flexible vacuum conduit tube 24 is attached to the plenum at one end 16 by means of coupling 22 and to a vacuum collection system at the other end 18 by means of coupling 20. Typically medical procedural areas where liquids are anticipated to be expelled are fitted with vacuum collection systems for this specific purpose.

Figure 3:
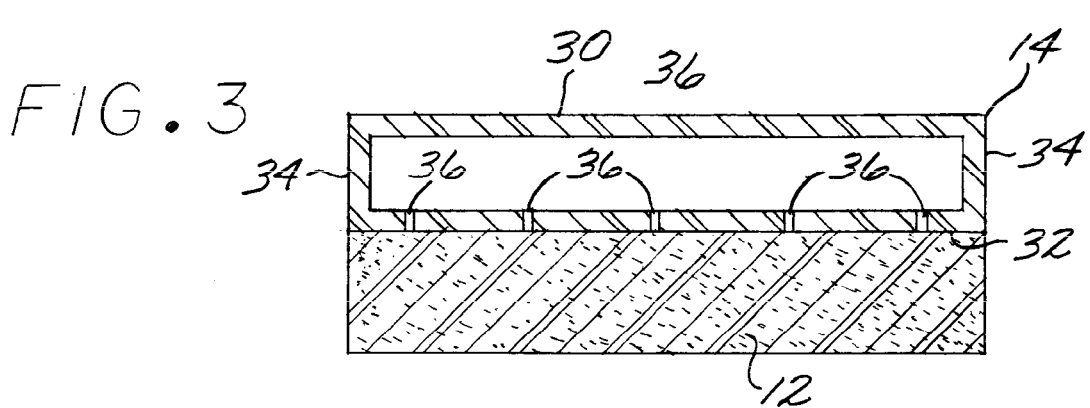
FIG. 3 is a drawing in section with portions broken away of the liquid removal apparatus taken along Line 3-3 of FIG. 1.
Figure 4:
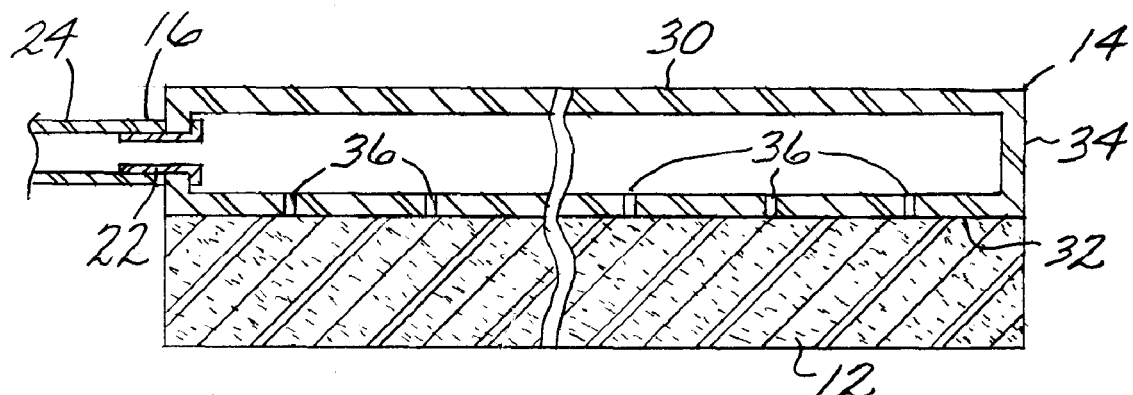
FIG. 4 is a drawing in section with portions broken away of the liquid removal apparatus taken along Line 4-4 of FIG. 1.

In sectional views of the preferred embodiment, in FIGS. 3-4, the plenum may be defined by an elongated rectangular box having an interior volume defined by a top plate 30 and a bottom plate 32 and a plurality of support members 34 integral to plenum. In this embodiment the support members 34 form side edges of the plenum. A plurality of perforations 36 are formed in the bottom plate 32 to allow air and liquid communication between the exterior of the plenum and the interior volume of the plenum. The top and bottom plates are closely spaced so as to minimize the volume of the plenum whilst maintaining functionality of the apparatus.

The number, the size and the locations of the perforations 36 in the bottom plate of the plenum may vary. Experiments have shown that perforations in the form of circular holes having a diameter generally between 0.005 and 0.060 inches and preferably about 0.020 inches collectively limit the total leakage of air into the plenum when no liquid is present in the absorptive pad while providing adequate liquid communication into the plenum.

Alternatively, a slot may be cut in the base plate of the plenum wherein a tape with perforations may be adhesively attached to the plenum base plate to cover the slot and restoring the plenum integrity. This has an advantage when perforation fabrication is more efficiently conducted on a tape rather than directly on the plenum.

An absorptive wicking pad 12 having the general dimensions of the bottom plate 32 and a thickness is fixed to the bottom plate 32 of the plenum 14 so as to cover all of the plurality of perforations in the plate. The means for fixing the absorptive wicking pad 12 in position to the bottom plate 32 includes an adhesive means applied to the bottom plate 32 before positioning the absorptive wicking pad. The adhesive is preferably a glue having properties that circumvent clogging when dry or cured.

The absorptive wicking pad 12 has properties consistent with the ability to draw or soak up liquids to be removed from the surface through a capillary effect and to hold the liquid within the material. The material should have a porosity sufficient to permit liquid flow through the material when drawn by a vacuum. The absorptive wicking material QUICK-WICK, from Avec Scientific Design, has been found to perform suitably. Other materials including porous foams and various textiles may also be used. The absorptive wicking pad has a thickness preferably or 0.125 inches or greater. It is essential that the absorptive wicking pad be constructed of one piece of material as any discontinuity in the material seriously impairs the capillary effect.

Referring to FIG. 1 and FIG. 4, a flexible vacuum conduit tube 24 having a distal end 18 and a proximal end 16 is coupled to the plenum 14 so as to be in direct vacuum communication with the plenum 14. As shown in FIG. 4, coupling 22 forms the distal end of the tube 24 and is so secured to the plenum 14 as to prevent leakage of air or liquid at the connection. Coupling adapter 20 forms the distal end 18 of the tube is fashioned to secure to standard vacuum manifold systems on vacuum collection systems.

During operation, the vacuum desirably drawn to effectuate efficient liquid transport through the apparatus is in the order of 200 millimeters of water. Vacuums as low as 50 millimeters of water can be used, but below about 100 millimeters of water efficiency drops substantially. Generally the vacuum magnitude is preselected in the operating room; however if the vacuum magnitude is adjustable it may be adjusted during operation to maximize performance.

Figure 5:
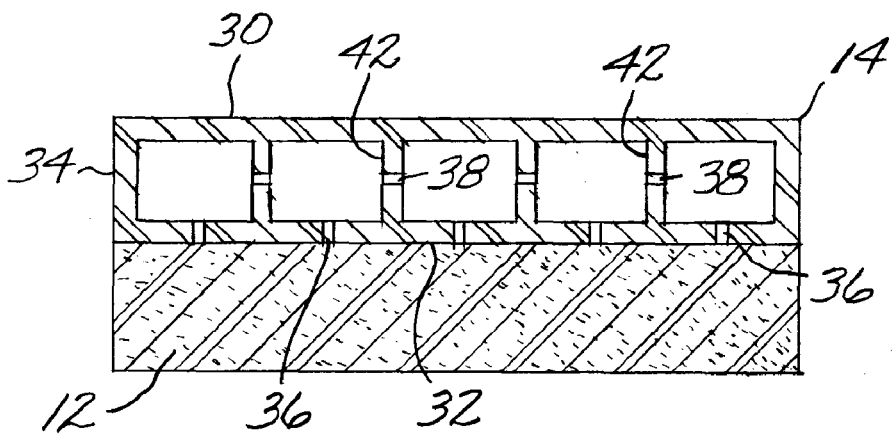
FIG. 5 is a drawing in section with portions broken away of a second embodiment of the liquid removal apparatus taken along Line 3-3 of FIG. 1 wherein the plenum is a corrugated material.
Figure 6:
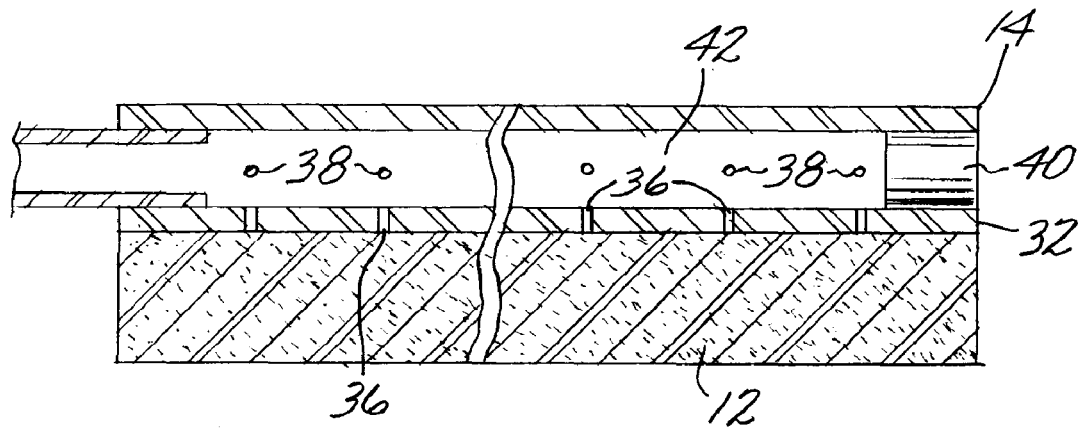
FIG. 6 is a drawing in section with portions broken away of a second embodiment of the liquid removal apparatus taken along Line 4-4 of FIG. 1 wherein the plenum is a corrugated material.
Figure 7:
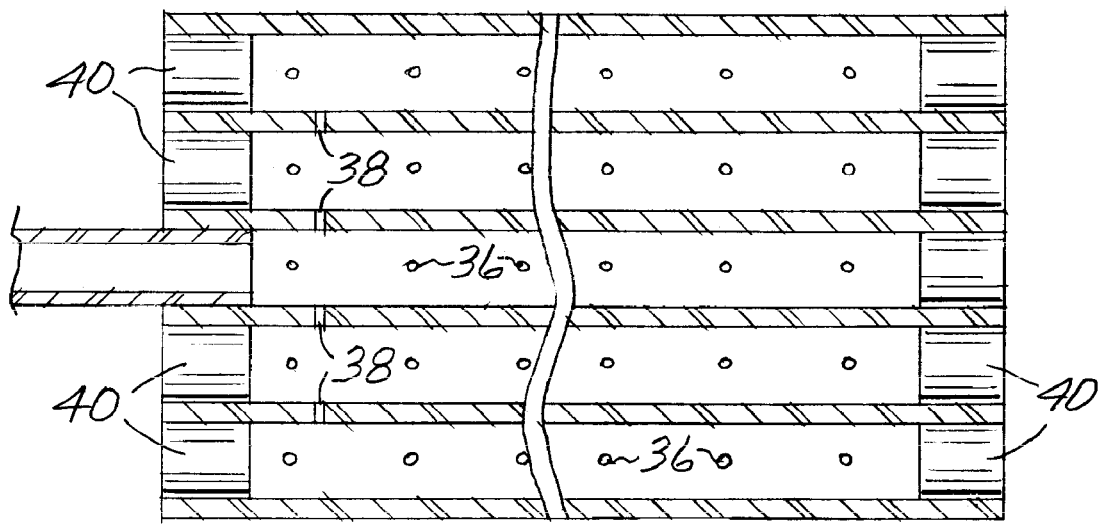
FIG. 7 is a drawing in section from a top plan view of a further embodiment of the liquid removal apparatus wherein the plenum volume is defined by passage channels.

In sectional views of a second embodiment, in FIGS. 5-7, the plenum interior volume may further be defined by additional support members 42 also integral to the plenum 14, forming passage channels by support members 42 located in the interior of the plenum. This has the advantage that the plenum 14 may be constructed of standard corrugated plastic panel. Passage channels are in direct air and liquid communication with each other through openings 38. This second embodiment shows the use of corrugated plastic panels with the passage channel ends defined by sealing plug 40.

Figure 8:
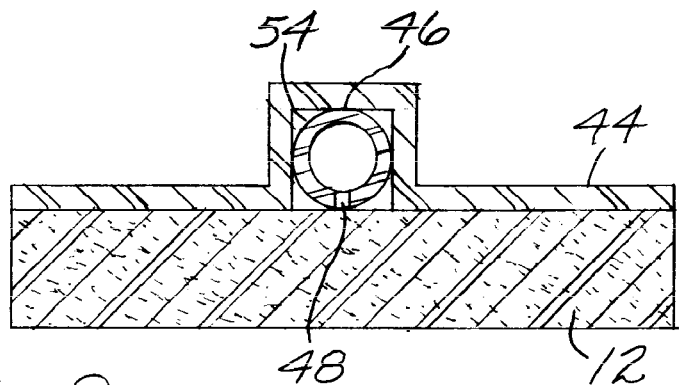
FIG. 8 is a drawing in section with portions broken away of a third embodiment of the liquid removal apparatus taken along Line 3-3 of FIG. 1 wherein the plenum is generally cylindrical.
Figure 9:
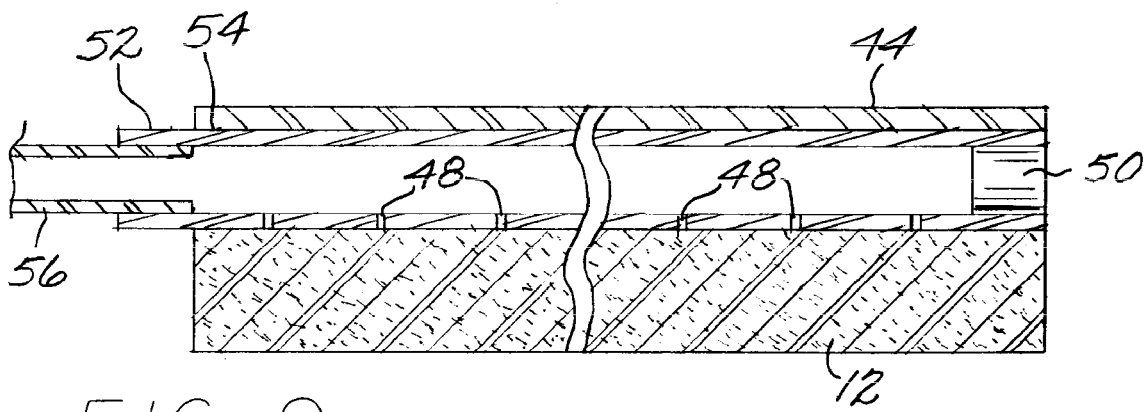
FIG. 9 is a drawing in section with portions broken away of a third embodiment of the liquid removal apparatus taken along Line 4-4 of FIG. 1 wherein the plenum is generally cylindrical.

A third embodiment in sectional view in FIGS. 8-9, shows an alternate form of plenum effectuating similar functionality to other embodiments wherein the plenum 54 is defined by a cylindrical element 46 such as a tube or pipe further defining the interior volume of the plenum 54 and having an outer surface and a length. The cylindrical element of the plenum is perforated along a length of the cylindrical element wherein the perforations 48 have dimensions the same as for other embodiments. The plenum is cylindrical element 46 is sealed at one end by sealing plug 50 and secured to effectuate direct vacuum connectivity with a coupling adapter 52 on the end of a vacuum conduit tube 56. The opposing end of the flexible vacuum conduit tube 56 is in direct vacuum connectivity with the vacuum collection system as in other embodiments. The plenum is retained by a support base 44 giving rigidity to the apparatus. Absorptive wicking pad 12 is fixed to the plenum 54 and the support base 44 by an adhesive means with the perforations 48 in direct contact with the absorptive wicking pad 12.

The method for liquid removal from surfaces then is accomplished by positioning the present invention with the exposed absorptive wicking pad side onto the surface where the liquid is to be removed resides. The apparatus is secured to the vacuum collection system which is then activated. The pad wicks the liquid into the pad. The vacuum present in the plenum draws liquids collected into the plenum and the drawn vacuum from the vacuum collection system transports entrained liquid and air from the apparatus.

Contact between the absorptive wicking pad and the surface where the liquid resides is essential for efficient operation of the apparatus. The plenum is so engineered to be flexible along the longitudinal dimension such that the plenum contours to the irregularities of surfaces such as floors. The plenum is further so engineered to be rigid along the lateral dimension such that the plenum can be pushed for positioning and so that the entire apparatus acts as a barrier to pooling liquids without deforming.

The material used to fabricate the plenum is preferably plastic however, waxed cardboard or metal sheeting are also suitable or other materials sufficient to maintain latitudinal rigidity and flexibility along the longitudinal axis of the plenum and imperviousness to air and liquid leakage.

When the apparatus has been constructed in the preferred configuration and operated according to the parameters noted above, it has been found to operate quietly during operation and highly effective in removing standing liquids.

What is claimed is:

1. A disposable liquid removal apparatus for evacuating liquids for use during medical procedures to remove liquids from surfaces including floors, responsively to a drawn vacuum of preselected magnitude and contacting the surface, comprising;

a plenum defined by an elongated rectangular crush resistant box element constructed from corrugated panel, capable of containing a vacuum, defining an interior volume by a top and bottom plate with a plurality of support members attached to the bottom of the top plate and the top of the bottom plate of the panel forming passage channels along the longitudinal axis of the plenum and within the plenum, each having ends, with one passage channel end open to receive a tube with the remainder of the passage channel ends sealed by plugs with the passage channels in direct air and fluid communication with one another by means of openings in adjacent support members, said bottom plate of plenum has a plurality of circular perforations having a diameter between 0.005 and 0.060 inches in fluid communication with the plenum, wherein the total leakage of air into the plenum is collectively limited by the perforations, an absorptive wicking pad having a top, a bottom, dimensions generally of the bottom plate, and a thickness, and constructed from a material having wicking and capillary properties commensurate with drawing and transporting liquids from a surface having a porosity sufficient to permit liquid flow through the pad when drawn by a vacuum from the top of the pad, with the top of the pad fixed to the bottom of the bottom plate of the plenum so as to cover and to be in liquid communication with all perforations in the bottom plate, and the bottom of the pad directly contacting the surface from which liquid is to be removed; and a flexible vacuum conduit tube having a distal end and a proximal end wherein the proximal end is coupled with the open passage channel end of the plenum for receiving a tube and the distal end is coupled to; and, is in direct fluid and liquid communication with a vacuum collection system having a drawn vacuum capable of drawing and collecting expelled fluids and designed for applications in medical procedural areas.

2. The disposable liquid removal apparatus of claim 1, wherein the top of the pad is fixed to the bottom of the bottom plate by adhesive glue having properties that circumvent clogging the circular perforations in the bottom plate when cured.

3. The disposable liquid remove apparatus of claim 1, wherein the vacuum collection system has a vacuum draw capability selected and the plurality of circular perforations selected in size and number so as to collectively limit the total leakage of air into the plenum when no liquid is present in the pad so as to sustain a pressure of 200 millimeters of water in the plenum when drawn.

4. The disposable liquid remove apparatus of claim 1, wherein the vacuum collection system has a vacuum draw capability selected and the plurality of circular perforations are selected in size and number so as to collectively to draw fluid through the pad at a pressure of 50 millimeters of water in the plenum.

5. The disposable liquid removal apparatus of claim 1, wherein the plenum corrugated panel is constructed of plastic.

6. The disposable liquid removal apparatus of claim 1, wherein the plenum corrugated panel is constructed of waxed cardboard.

7. The disposable liquid removal apparatus of claim 1, wherein the plenum corrugated panel is constructed of metal sheeting.

8. The disposable liquid removal apparatus of claim 1, wherein the pad has a thickness between the top and bottom equal to or greater than 0.125 inches and is constructed of one continuous piece of material.

9. The disposable liquid removal apparatus of claim 1, wherein the plenum has one passage channel.

10. The disposable liquid removal apparatus of claim 9, wherein the one passage channel is cylindrical.

11. The disposable liquid removal apparatus of claim 1, wherein the wicking pad material is porous foam having wicking properties.

12. The disposable liquid removal apparatus of claim 1, wherein the wicking pad material is textile having wicking properties.

* * * * *